United States Patent [19]

Boyle et al.

[11] Patent Number: 4,589,274

[45] Date of Patent: May 20, 1986

[54] METHOD AND APPARATUS FOR CONTINUOUSLY DETECTING AND MONITORING THE HYDROCARBON DEW-POINT OF A GAS

[75] Inventors: George J. Boyle; Frederick R. Pritchard, both of Chester, England

[73] Assignee: Shell Oil Company, Houston, Tex.

[21] Appl. No.: 645,199

[22] Filed: Aug. 29, 1984

[30] Foreign Application Priority Data

Aug. 30, 1983 [GB] United Kingdom ............... 8323260

[51] Int. Cl.⁴ ............................................. G01N 25/12
[52] U.S. Cl. ........................................ 73/29; 73/336.5
[58] Field of Search ...................... 73/29, 336.5, 336; 374/20, 16, 17, 18, 19

[56] References Cited

U.S. PATENT DOCUMENTS

| | | | |
|---|---|---|---|
| 3,528,278 | 9/1970 | Sterling | 73/336.5 |
| 3,552,186 | 1/1971 | Sproul | 73/29 |
| 3,890,828 | 6/1975 | Pleva | 73/29 |

*Primary Examiner*—Stephen A. Kreitman

[57] ABSTRACT

Methods and apparatus are provided for continuously detecting and monitoring the hydrocarbon dew point of a gas. A sample of the gas stream whose dew point is to be monitored is heated and/or cooled prior to detection by a dew point detector. The cooling of a first portion of a sample may be accomplished by a second portion of the sample which is removed prior to the dew point detector and allowed to expand to cool the first portion of the sample. The sample is normally cooled until the presence of condensate is detected in the gas by the dew point detector whereupon the sample gas is heated to above the dew point and the procedure of cooling and heating the gas stream occurs in a continuous manner.

6 Claims, 1 Drawing Figure

METHOD AND APPARATUS FOR CONTINUOUSLY DETECTING AND MONITORING THE HYDROCARBON DEW-POINT OF A GAS

BACKGROUND OF THE INVENTION

The invention relates to a method and apparatus for continuously detecting and monitoring the hydrocarbon dew-point or changes in the dew-point properties of a gas.

Presently, there is a need, both onshore and offshore, for a method and apparatus capable of continuously monitoring hydrocarbon dew-point and the amount of condensate produced, at or a little below the dew-point, from pipeline gas.

Dew-point detectors based upon the principle of detecting the presence of dew on a cooled surface, for example a mirror, are already available. Prismatic devices involving visible or infrared light can also be used which rely on the principle of total internal reflection in the absence of a liquid or other medium on the surface. The presence of liquid or other medium on the surface allows light to escape and reduces the intensity of the return beam. Such an imbalance can be used to signal dew-point when condensed liquid forms on the surface and the change in light intensity can be amplified to drive suitable indicating recorders and relays. See, for example, the dew-point detector disclosed in U.S. Pat. No. 3,528,278.

However, in order to obtain an accurate indication of the dew-point it is necessary to meet rigid requirements as to temperature and pressure and it will be necessary to present a gas sample to be investigated under controlled conditions to the detector.

SUMMARY OF THE INVENTION

Therefore, it is an object of the invention to provide a method and an apparatus for continuously detecting and monitoring the hydrocarbon dew-point or changes in the dew-point properties of a gas wherein the gas sample stream is presented to the detector under controlled conditions.

It is another object of the present invention to provide such a method and apparatus in which stoppage of the gas flow due to hydration or liquid formation is prevented.

The invention therefore provides a method for continuously detecting and monitoring the hydrocarbon dew-point or changes in the dew-point properties of a gas comprising the steps of supplying a gas sample to be investigated to a dew-point detector; progressively lowering the temperature of a portion of the sample gas stream to be investigated until the dew-point is reached, said temperature lowering step taking place prior to detection; detecting the presence of condensate within the flowing gas and subsequently heating the supply gas sample to above the dew-point and repeating the above-mentioned procedure of cooling and heating the gas stream continuously in a cyclical manner. The invention further provides an apparatus for continuously detecting and monitoring the hydrocarbon dew-point or changes in the dew-point properties of a gas comprising means adapted to supply a sample gas to be investigated to a dew-point detector, means adapted to cool and to heat the gas stream in a cyclical manner at determined points prior to detection and further comprising means adapted to detect the presence of condensate within the flowing gas. The invention has been based upon the fact that the gas stream to be investigated can be cooled to the dew-point by means of a controlled expansion to a constant temperature of a portion of said gas stream.

BRIEF DESCRIPTION OF THE DRAWINGS

The invention will now be described in more detail by way of example with reference to the accompanying drawing.

DETAILED DESCRIPTION OF THE PREFERRED EMBODIMENT

Figure 1:
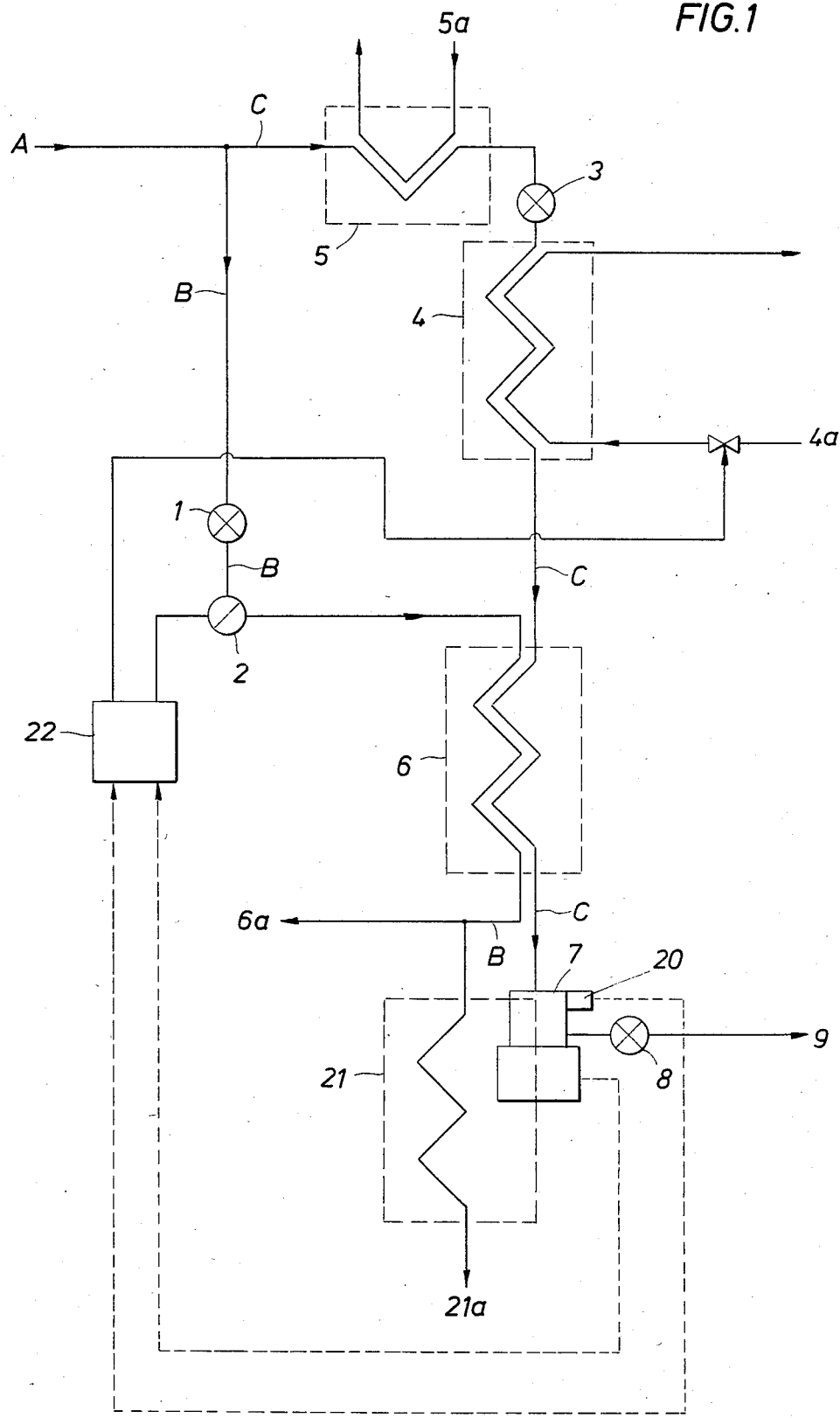
FIG. 1 represents schematically an arrangement of the dewpont monitor of the invention.

With reference to FIG. 1 a sample gas stream "A" to be investigated is split by any suitable means into at least two streams "B" and "C" respectively.

The first stream, "B", passes through a metering valve 1 and is expanded to a determined pressure, for example atmospheric pressure, through an oscillating valve 2, which allows a regulated volume of gas to rapidly expand at a controllable frequency. In an advantageous embodiment of the invention this valve 2 may be air-actuated and/or temperature-controlled by controller 22. The oscillating action prevents hydrates, which may form in the expansively cooled gas, from blocking the valve.

The second stream, "C", passes expansively through a pressure regulator 3 which controls the utimate pressure in detector cell 7. The stream "C" then passes through a heat exchanger 4 furnished with heating means 4a which may be, for example, hot water, low pressure steam or appropriate direct or indirect electrical heating. The flow of heating means is controlled by the dew-point detector control system and is only active when clearing the prism of condensate to raise the temperature of stream "C" above the dew-point.

A heat exchanger 5, with heating means 5a as described for the heat exchanger 4, may be used if the sample gas stream "A" is already close to the dew-point.

The sample gas stream "C" is cooled by the expanded, cold, oscillating gas stream "B" in a cooling chamber 6 which is vented at 6a. Subsequently the cold gas stream "C" enters the detector cell 7 (schematically shown) and is vented at 9 through a flow control means 8. The cooling process is continued until the dew-point is reached.

Since dew-point detectors as such are known, as already disclosed earlier, they will not be described in detail. The progressive reduction in temperature can be indicated in any way suitable for the purpose, for example a temperature detector 20, adjacent to the detector cell 7. The temperature at which the detector 7 indicates the presence of condensate in the dew-point. It will be appreciated that the detector 7 can be connected in any suitable way to suitable signal indicators, for example recorders.

When the dew-point has been reached the (air) supply to the oscillating valve 2 is cut off and a flow of heating means 4a to heater 4 is started by controller 22; the temperature of the system rises again and when the detector 7 response shows that the detector 7 is free of condensate the cooling cycle is restarted. The above procedure of cooling and heating the gas stream is repeated continuously in a cyclical manner prior to the detection step. It will be appreciated that the rate of cooling using gas stream "B" may be adjusted with the oscillating valve 2 to suit the characteristics of different gases "A".

In an advantageous embodiment of the invention the pressure of the sampling pipeline gas is at about 70 bars and the measuring dewpoint is at 28.6 bars, using a flow of about 3 m$^3$/h of gas through the detector.

It will further be appreciated that any cycle times suitable for the purpose can be used.

In an advantageous embodiment of the invention cycle times of about 20 minutes were observed. Cycle time is primarily a function of the heat capacity of the heater 4 and the detector body 7 and by suitable modifications of these components cycle times of 6–10 minutes are used in other advantageous embodiments of the invention.

In another advantageous embodiment the gas sample can be heated, if desired, after the expansion step.

It is also possible to use the gas vented from the cooling chamber 6 to assist the cooling of the detector 7 by heat exchanger 21 and vent line 21a.

A further advantage of the invention is that the light for the dew-point detection system may be carried via light guides from a safe area remote from hazardous areas e.g. oil rigs, production platforms, gas separation/treatment plants and the like. Similarly, all electrical switching and electrically powered components such as recorders, solenoid valves, printers etc. can be located remotely from the sample conditioning and dew-point detection module which can be located in a hazardous area.

Various modifications of the invention will become apparent to those skilled in the art from the foregoing description and accompanying drawings. Such modifications are intended to fall within the scope of the appended claims.

What is claimed is:

1. A method for monitoring the dew-point of a gas, comprising:
   providing a sample of said gas;
   dividing said sample into a first and second portion and expanding said second portion to cool said first portion;
   cooling a first portion of said sample until condensate is formed therein;
   detecting said condensate in said first portion of said sample;
   warming said first portion of said sample until condensate is removed therefrom;
   detecting said removal of said condensate from said first portion of said sample; and thereafter
   alternately cooling and warming said first portion of said sample in response to the detection of absence or presence of condensate in said first portion of said sample.

2. The method of claim 1, wherein said expanding of said second portion is substantially cyclical and has a predetermined regular interval.

3. The method of claim 1, further comprising:
   providing a controller to control said expanding of said second portion of said sample;
   detecting the temperature of said first portion of said sample and operating said controller in functional relationship to said temperature of said first portion of said sample and detection of absence or presence of condensate in said first portion of said sample.

4. Apparatus for monitoring the dew-point of a gas, comprising:
   a detector means for detecting condensate in said gas;
   means for cooling a first portion of said gas and supplying said cooled first portion to said detector means;
   means for dividing said gas into a first and second portion and supplying said second portion of said gas to said means for cooling;
   means for heating said first portion of said gas; and
   controller means for said means for cooling and said means for heating responsive to said detector means.

5. The apparatus of claim 4, wherein said means for cooling expands said second portion of said gas to cool said first portion of said gas.

6. The apparatus of claim 5, wherein said expanding of said second portion of said gas is substantially regular and periodic.

* * * * *